(12) United States Patent
Poppe et al.

(10) Patent No.: US 10,966,829 B2
(45) Date of Patent: Apr. 6, 2021

(54) MEDICAL DEVICE SHAFT INCLUDING A LINER

(71) Applicant: BOSTON SCIENTIFIC SCIMED, INC., Maple Grove, MN (US)

(72) Inventors: Kevin Robert Poppe, New Brighton, MN (US); Daniel J. Foster, Lino Lakes, MN (US); Bradley S. Swehla, Eagan, MN (US); Christopher Jay Scheff, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 65 days.

(21) Appl. No.: 15/921,005

(22) Filed: Mar. 14, 2018

(65) Prior Publication Data
US 2018/0263771 A1 Sep. 20, 2018

Related U.S. Application Data

(60) Provisional application No. 62/471,100, filed on Mar. 14, 2017.

(51) Int. Cl.
*A61F 2/24* (2006.01)
*A61F 2/966* (2013.01)
(Continued)

(52) U.S. Cl.
CPC ............ *A61F 2/2436* (2013.01); *A61F 2/966* (2013.01); *A61M 25/0032* (2013.01);
(Continued)

(58) Field of Classification Search
CPC ...... A61F 2230/0008; A61F 2230/0017; A61F 2/2436; A61F 2/966; A61M 2025/0004;
(Continued)

(56) References Cited

U.S. PATENT DOCUMENTS 3,674,014 A 7/1972 Tillander
4,798,598 A 1/1989 Bonello et al.
(Continued)

FOREIGN PATENT DOCUMENTS

EP 0778040 A2 6/1997
EP 2455128 A2 5/2013
(Continued)

OTHER PUBLICATIONS

International Search Report and Written Opinion dated Mar. 2, 2018 for International Application No. PCT/US2017/062113.
(Continued)

*Primary Examiner* — Kathleen S Holwerda
*Assistant Examiner* — Brooke Labranche
(74) *Attorney, Agent, or Firm* — Seager, Tufte & Wickhem LLP

(57) ABSTRACT

Medical devices and methods for making and using medical devices are disclosed. An example delivery system for an implantable medical device includes an inner shaft having a proximal end region, a distal end region, a non-circular lumen extending therethrough. The delivery system also includes a tension resistance member extending at least partially between the proximal end region and the distal end region, a deployment catheter disposed along the outer surface of the shaft, and an actuation shaft disposed within the non-circular lumen. Further, the actuation shaft is coupled to the implantable medical device and translation of the actuation shaft shifts the implantable medical device from a first position to a second position.

14 Claims, 5 Drawing Sheets

(51) Int. Cl.
*A61M 25/00* (2006.01)
*A61M 25/01* (2006.01)
*A61M 25/09* (2006.01)

(52) U.S. Cl.
CPC ............... *A61F 2230/0008* (2013.01); *A61F 2230/0017* (2013.01); *A61M 25/0023* (2013.01); *A61M 25/0147* (2013.01); *A61M 25/09* (2013.01); *A61M 2025/0004* (2013.01); *A61M 2025/0037* (2013.01)

(58) Field of Classification Search
CPC ...... A61M 2025/0037; A61M 25/0023; A61M 25/0032; A61M 25/0147; A61M 25/09
See application file for complete search history.

(56) References Cited

U.S. PATENT DOCUMENTS

| | | | |
|---|---|---|---|
| 4,955,384 A | 9/1990 | Taylor et al. | |
| 4,985,022 A | 1/1991 | Fearnot et al. | |
| 4,998,923 A | 3/1991 | Samson et al. | |
| 5,003,989 A | 4/1991 | Taylor et al. | |
| 5,095,915 A | 3/1992 | Engelson | |
| 5,315,996 A | 5/1994 | Lundquist | |
| 5,406,960 A | 4/1995 | Corso, Jr. | |
| 5,437,288 A | 8/1995 | Schwartz et al. | |
| 5,570,701 A | 11/1996 | Ellis et al. | |
| 5,599,492 A | 2/1997 | Engelson | |
| 5,746,701 A | 5/1998 | Noone | |
| 5,749,837 A | 5/1998 | Palermo et al. | |
| 5,769,796 A | 6/1998 | Palermo et al. | |
| 5,772,609 A | 6/1998 | Nguyen et al. | |
| 5,776,080 A | 7/1998 | Thome et al. | |
| 5,833,632 A | 11/1998 | Jacobsen et al. | |
| 5,902,254 A | 5/1999 | Magram | |
| 5,931,830 A | 8/1999 | Jacobsen et al. | |
| 5,951,494 A | 9/1999 | Wang et al. | |
| 6,001,068 A | 12/1999 | Uchino et al. | |
| 6,017,319 A | 1/2000 | Jacobsen et al. | |
| 6,139,510 A | 10/2000 | Palermo | |
| 6,273,876 B1 | 8/2001 | Klima et al. | |
| 6,398,776 B1 * | 6/2002 | Sekino | A61M 25/0144 600/149 |
| 6,606,921 B2 | 8/2003 | Noetzold | |
| 6,739,787 B1 | 5/2004 | Bystrom | |
| 6,918,882 B2 | 7/2005 | Skujins et al. | |
| 6,921,397 B2 | 7/2005 | Corcoran et al. | |
| 7,055,656 B2 | 6/2006 | Drew | |
| 7,074,197 B2 | 7/2006 | Reynolds et al. | |
| 7,338,495 B2 | 3/2008 | Adams | |
| 7,413,563 B2 | 8/2008 | Corcoran et al. | |
| 7,533,906 B2 | 5/2009 | Luettgen et al. | |
| 7,540,865 B2 | 6/2009 | Griffin et al. | |
| 7,579,550 B2 | 8/2009 | Dayton et al. | |
| 7,618,379 B2 | 11/2009 | Reynolds et al. | |
| 7,625,364 B2 | 12/2009 | Corcoran et al. | |
| 7,780,611 B2 | 8/2010 | Griego et al. | |
| 7,784,376 B2 | 8/2010 | Wen | |
| 7,824,345 B2 | 11/2010 | Euteneuer et al. | |
| 7,841,994 B2 | 11/2010 | Skujins et al. | |
| 7,850,623 B2 | 12/2010 | Griffin et al. | |
| 7,854,109 B2 | 12/2010 | Zubiate et al. | |
| 7,914,466 B2 | 3/2011 | Davis et al. | |
| 7,914,467 B2 | 3/2011 | Layman et al. | |
| 7,918,080 B2 | 4/2011 | Zubiate et al. | |
| 7,993,286 B2 | 8/2011 | Reynolds et al. | |
| 8,022,331 B2 | 9/2011 | Reynolds et al. | |
| 8,047,236 B2 | 11/2011 | Perry | |
| 8,048,004 B2 | 11/2011 | Davis et al. | |
| 8,048,060 B2 | 11/2011 | Griffin et al. | |
| 8,099,939 B2 | 1/2012 | Zubiate et al. | |
| 8,100,031 B2 | 1/2012 | Zubiate et al. | |
| 8,105,246 B2 | 1/2012 | Voeller et al. | |
| 8,124,876 B2 | 2/2012 | Dayton et al. | |
| 8,137,293 B2 | 3/2012 | Zhou et al. | |
| 8,157,751 B2 | 4/2012 | Adams et al. | |
| 8,182,465 B2 | 5/2012 | Griffin et al. | |
| 8,192,422 B2 | 6/2012 | Zubiate et al. | |
| 8,197,419 B2 | 6/2012 | Field et al. | |
| 8,231,551 B2 | 7/2012 | Griffin et al. | |
| 8,257,279 B2 | 9/2012 | Davis et al. | |
| 8,292,829 B2 | 10/2012 | Griego et al. | |
| 8,317,777 B2 | 11/2012 | Zubiate et al. | |
| 8,376,865 B2 | 2/2013 | Forster et al. | |
| 8,376,961 B2 | 2/2013 | Layman et al. | |
| 8,377,035 B2 | 2/2013 | Zhou et al. | |
| 8,397,481 B2 | 3/2013 | Zubiate et al. | |
| 8,409,114 B2 | 4/2013 | Parins | |
| 8,414,506 B2 | 4/2013 | Reynolds et al. | |
| 8,425,408 B2 | 4/2013 | Boulais et al. | |
| 8,443,692 B2 | 5/2013 | Zubiate et al. | |
| 8,449,526 B2 | 5/2013 | Snyder et al. | |
| 8,459,138 B2 | 6/2013 | Zubiate et al. | |
| 8,475,366 B2 | 7/2013 | Boulais et al. | |
| 8,485,992 B2 | 7/2013 | Griffin et al. | |
| 8,535,219 B2 | 9/2013 | Smith et al. | |
| 8,535,243 B2 | 9/2013 | Shireman | |
| 8,551,020 B2 | 10/2013 | Chen et al. | |
| 8,551,021 B2 | 10/2013 | Voeller et al. | |
| 8,556,914 B2 | 10/2013 | Vrba | |
| 8,608,648 B2 | 12/2013 | Banik et al. | |
| 8,622,894 B2 | 1/2014 | Banik et al. | |
| 8,636,716 B2 | 1/2014 | Griffin et al. | |
| 8,656,697 B2 | 2/2014 | Zubiate et al. | |
| 8,677,602 B2 | 3/2014 | Dayton et al. | |
| 8,758,268 B2 | 6/2014 | Bown et al. | |
| 8,784,337 B2 | 7/2014 | Voeller et al. | |
| 8,795,202 B2 | 8/2014 | Northrop et al. | |
| 8,795,254 B2 | 8/2014 | Layman et al. | |
| 8,821,477 B2 | 9/2014 | Northrop et al. | |
| 8,833,197 B2 | 9/2014 | Zubiate et al. | |
| 8,845,552 B2 | 9/2014 | Greigo et al. | |
| 8,864,654 B2 | 10/2014 | Kleiner et al. | |
| 8,870,790 B2 | 10/2014 | Davis et al. | |
| 8,900,163 B2 | 12/2014 | Jacobsen et al. | |
| 8,915,865 B2 | 12/2014 | Jacobsen et al. | |
| 8,932,235 B2 | 1/2015 | Jacobsen et al. | |
| 8,936,558 B2 | 1/2015 | Jacobsen et al. | |
| 8,939,916 B2 | 1/2015 | Jacobsen et al. | |
| 8,945,096 B2 | 2/2015 | Zubiate et al. | |
| 9,005,114 B2 | 4/2015 | Zubiate et al. | |
| 9,011,318 B2 | 4/2015 | Choset et al. | |
| 9,023,011 B2 | 5/2015 | Griffin et al. | |
| 9,072,874 B2 | 7/2015 | Northrop et al. | |
| 9,370,432 B2 | 6/2016 | Zubiate et al. | |
| 9,375,234 B2 | 6/2016 | Vrba | |
| 9,386,911 B2 | 7/2016 | Zubiate et al. | |
| 9,387,308 B2 | 7/2016 | Hinchliffe et al. | |
| 9,387,309 B2 | 7/2016 | Parodi et al. | |
| 9,402,682 B2 | 8/2016 | Worrell et al. | |
| 2001/0037141 A1 | 11/2001 | Yee et al. | |
| 2003/0069520 A1 | 4/2003 | Skujins et al. | |
| 2003/0069521 A1 | 4/2003 | Reynolds et al. | |
| 2004/0220499 A1 | 11/2004 | Griego et al. | |
| 2004/0243143 A1 | 12/2004 | Corcoran et al. | |
| 2005/0080400 A1 | 4/2005 | Corcoran et al. | |
| 2005/0090848 A1 | 4/2005 | Adams | |
| 2005/0267444 A1 | 12/2005 | Griffin et al. | |
| 2006/0111615 A1 | 5/2006 | Danitz et al. | |
| 2006/0122537 A1 | 6/2006 | Reynolds et al. | |
| 2006/0179966 A1 | 8/2006 | Kuo | |
| 2006/0189896 A1 | 8/2006 | Davis et al. | |
| 2007/0049902 A1 | 3/2007 | Griffin et al. | |
| 2007/0066900 A1 | 3/2007 | O'Keeffe | |
| 2007/0083132 A1 | 4/2007 | Sharrow | |
| 2007/0100285 A1 | 5/2007 | Griffin et al. | |
| 2007/0114211 A1 | 5/2007 | Reynolds et al. | |
| 2007/0135734 A1 | 6/2007 | Reynolds et al. | |
| 2007/0233043 A1 | 10/2007 | Dayton et al. | |
| 2007/0244414 A1 | 10/2007 | Reynolds et al. | |
| 2008/0064989 A1 | 3/2008 | Chen et al. | |
| 2008/0077119 A1 | 3/2008 | Snyder et al. | |
| 2008/0194994 A1 | 8/2008 | Bown et al. | |
| 2008/0205980 A1 | 8/2008 | Zubiate et al. | |

(56) References Cited

U.S. PATENT DOCUMENTS

| | | |
|---|---|---|
| 2008/0245173 A1 | 10/2008 | Schwerin et al. |
| 2008/0262474 A1 | 10/2008 | Northrop |
| 2009/0036833 A1 | 2/2009 | Parins |
| 2009/0043228 A1 | 2/2009 | Northrop et al. |
| 2009/0043283 A1 | 2/2009 | Turnlund et al. |
| 2009/0143768 A1 | 6/2009 | Parodi et al. |
| 2009/0156999 A1 | 6/2009 | Adams et al. |
| 2009/0171151 A1 | 7/2009 | Choset et al. |
| 2009/0312606 A1 | 12/2009 | Dayton et al. |
| 2010/0063480 A1 | 3/2010 | Shireman |
| 2010/0076266 A1 | 3/2010 | Boulais et al. |
| 2010/0080892 A1 | 4/2010 | O'Brien et al. |
| 2010/0145308 A1 | 6/2010 | Layman et al. |
| 2010/0249655 A1 | 9/2010 | Lemon |
| 2010/0286566 A1 | 11/2010 | Griffin et al. |
| 2010/0294071 A1 | 11/2010 | Zubiate et al. |
| 2010/0305475 A1 | 12/2010 | Hinchliffe et al. |
| 2011/0056320 A1 | 3/2011 | Zubiate et al. |
| 2011/0082443 A1 | 4/2011 | Griffin et al. |
| 2011/0152613 A1 | 6/2011 | Zubiate et al. |
| 2011/0184241 A1 | 7/2011 | Zubiate et al. |
| 2011/0257478 A1 | 10/2011 | Kleiner et al. |
| 2012/0041411 A1* | 2/2012 | Horton ............ A61M 25/0026 604/500 |
| 2012/0160537 A1 | 6/2012 | Wen |
| 2012/0265134 A1* | 10/2012 | Echarri ............ A61M 25/0032 604/95.05 |
| 2013/0123796 A1 | 5/2013 | Sutton et al. |
| 2013/0123912 A1 | 5/2013 | Tung et al. |
| 2014/0235361 A1 | 8/2014 | Forster et al. |
| 2018/0140323 A1 | 5/2018 | Foster et al. |

FOREIGN PATENT DOCUMENTS

| | | |
|---|---|---|
| JP | 2012223578 A | 11/2012 |
| JP | 2013524943 A | 6/2013 |
| JP | 5575840 B2 | 8/2014 |
| JP | 2015501680 A | 1/2015 |
| WO | 2006041612 A2 | 4/2006 |
| WO | 2006073581 A2 | 7/2006 |
| WO | 2011133486 A1 | 10/2011 |

OTHER PUBLICATIONS

International Search Report and Written Opinion dated May 22, 2018 for International Application No. PCT/US2018/022371.

* cited by examiner

//MEDICAL DEVICE SHAFT INCLUDING A LINER

CROSS-REFERENCE TO RELATED APPLICATIONS

This application claims the benefit of priority under 35 U.S.C. § 119 to U.S. Provisional Application Ser. No. 62/471,100, filed Mar. 14, 2017, the entirety of which is incorporated herein by reference.

TECHNICAL FIELD

The present disclosure pertains to medical devices, and methods for manufacturing medical devices. More particularly, the present disclosure pertains to medical devices including a reduced profile inner liner.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example delivery system for an implantable medical device includes an inner shaft having a proximal end region, a distal end region, a non-circular lumen extending therethrough. The delivery system also includes a tension resistance member extending at least partially between the proximal end region and the distal end region, a deployment catheter disposed along the outer surface of the shaft, and an actuation shaft disposed within the non-circular lumen. Further, the actuation shaft is coupled to the implantable medical device and translation of the actuation shaft shifts the implantable medical device from a first position to a second position.

Alternatively or additionally to any of the embodiments above, wherein the implantable medical device includes an implantable heart valve.

Alternatively or additionally to any of the embodiments above, wherein the inner shaft includes a pair of tension resistance members disposed along opposite sides of the inner shaft.

Alternatively or additionally to any of the embodiments above, further comprising a pair of actuation shafts disposed within the non-circular lumen, and wherein the non-circular lumen is designed to limit twisting of the actuation shafts within the lumen.

Alternatively or additionally to any of the embodiments above, wherein the inner shaft is configured to rotate, translate or both rotate and translate relative to the deployment catheter.

Alternatively or additionally to any of the embodiments above, further comprising a first tubular member extending within the non-circular lumen, and wherein the first tubular member is designed to accept a guidewire extending therein.

Alternatively or additionally to any of the embodiments above, further comprising a second tubular member extending within the non-circular lumen, and wherein actuation shaft extends within the second tubular member.

Alternatively or additionally to any of the embodiments above, wherein the non-circular lumen is designed to limit twisting of the first tubular member and the second tubular member.

Alternatively or additionally to any of the embodiments above, wherein the tension resistance member includes a metallic wire.

Alternatively or additionally to any of the embodiments above, wherein the tension resistance member includes a polymer.

Another example delivery system for an implantable heart valve, comprising:
  an inner shaft having a distal end region, an ovular lumen extending therethrough, and a tension resistance member extending at least partially between the proximal end region and the distal end region;
  a deployment catheter disposed along the outer surface of the shaft; and
  an actuation shaft disposed within the ovular lumen;
  wherein the actuation shaft is coupled to the implantable medical device;
  wherein translation of the actuation shaft shifts the heart valve from a first position to a second position.

Alternatively or additionally to any of the embodiments above, wherein the inner shaft includes a pair of tension resistance members disposed along opposite sides of the inner shaft.

Alternatively or additionally to any of the embodiments above, further comprising a pair of actuation shafts disposed within the ovular lumen, and wherein the ovular lumen is designed to limit twisting of the actuation shafts within the ovular lumen.

Alternatively or additionally to any of the embodiments above, further comprising a first tubular member extending within the ovular lumen, and wherein the first tubular member is designed to accept a guidewire extending therein.

Alternatively or additionally to any of the embodiments above, further comprising a second tubular member extending within the ovular lumen, and wherein actuation shaft extends within the second tubular member.

Alternatively or additionally to any of the embodiments above, wherein the ovular lumen is designed to limit twisting of the first tubular member and the second tubular member.

Alternatively or additionally to any of the embodiments above, wherein the tension resistance member includes a metallic wire.

Alternatively or additionally to any of the embodiments above, wherein the tension resistance member includes a polymer.

A method for delivering an implantable medical device, the system comprising:
  advancing a medical device delivery system to a target site in the heart, the medical device delivery system including:
    an inner shaft having a proximal end region, a distal end region, a non-circular lumen extending therethrough, and a tension resistance member extending at least partially between the proximal end region and the distal end region;
    a deployment catheter disposed along the outer surface of the shaft;

an actuation shaft disposed within the non-circular lumen; and an implantable heart valve coupled to the actuation shaft;

retracting the deployment catheter relative to the inner shaft;

translating the actuation shaft relative to the inner shaft, wherein translating the actuation shaft shifts the implantable medical device from a collapsed position to a deployed position.

Alternatively or additionally to any of the embodiments above, wherein the implantable medical device includes an implantable heart valve.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
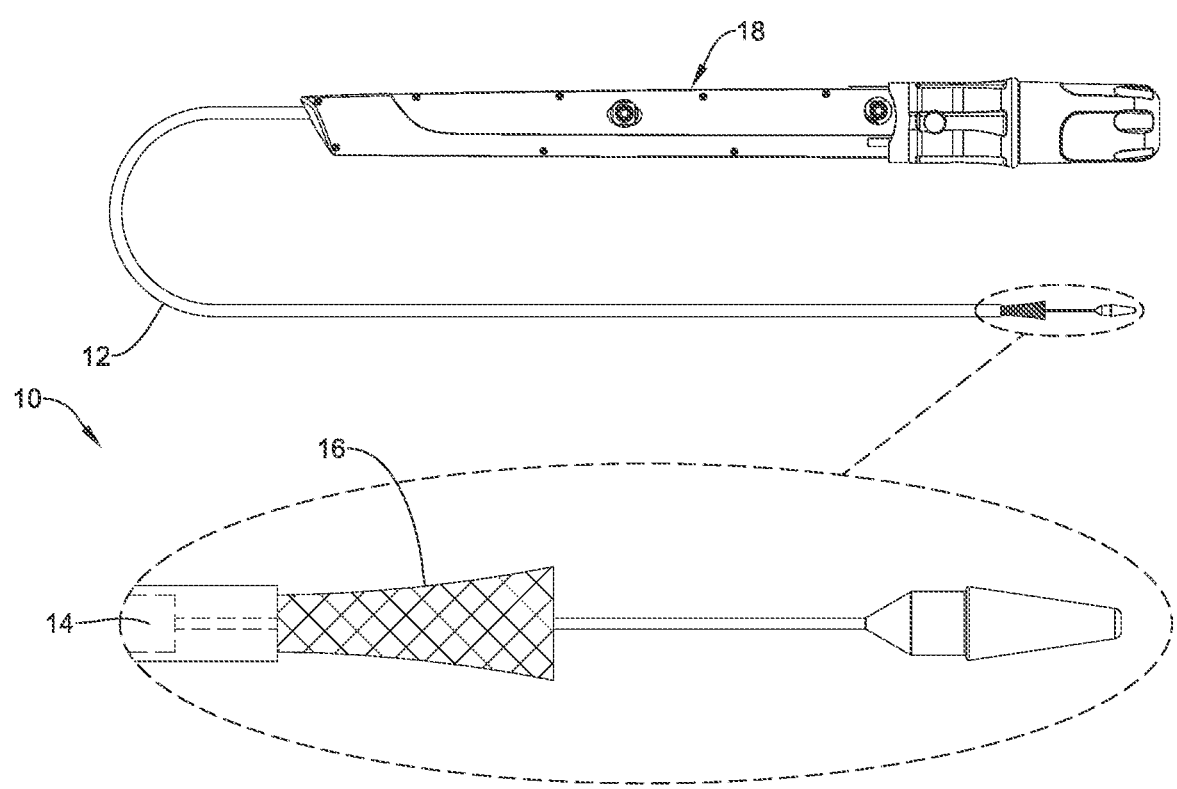
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16, such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 (a portion of which is shown in FIG. 1 in phantom line) extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 18 may be disposed at a proximal end of the outer sheath 12 and/or the inner catheter 14 and may include one or more actuation mechanisms associated therewith. In other words, a tubular member (e.g., the outer sheath 12, the inner catheter 14, etc.) may extend distally from the medical device handle 18. In general, the medical device handle 18 may be designed to manipulate the position of the outer sheath 12 relative to the inner catheter 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1 for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 18 in order to translate the medical implant 16 into a generally shortened and larger profile "deployed" configuration suitable for implantation within the anatomy. For example, in some instances the inner catheter (or components thereof) may be coupled to medical implant 16 whereby actuation of the inner catheter 14 relative to the outer sheath 12 and/or the medical implant 16 may deploy the medical device 16 within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system 10 may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

Figure 2:
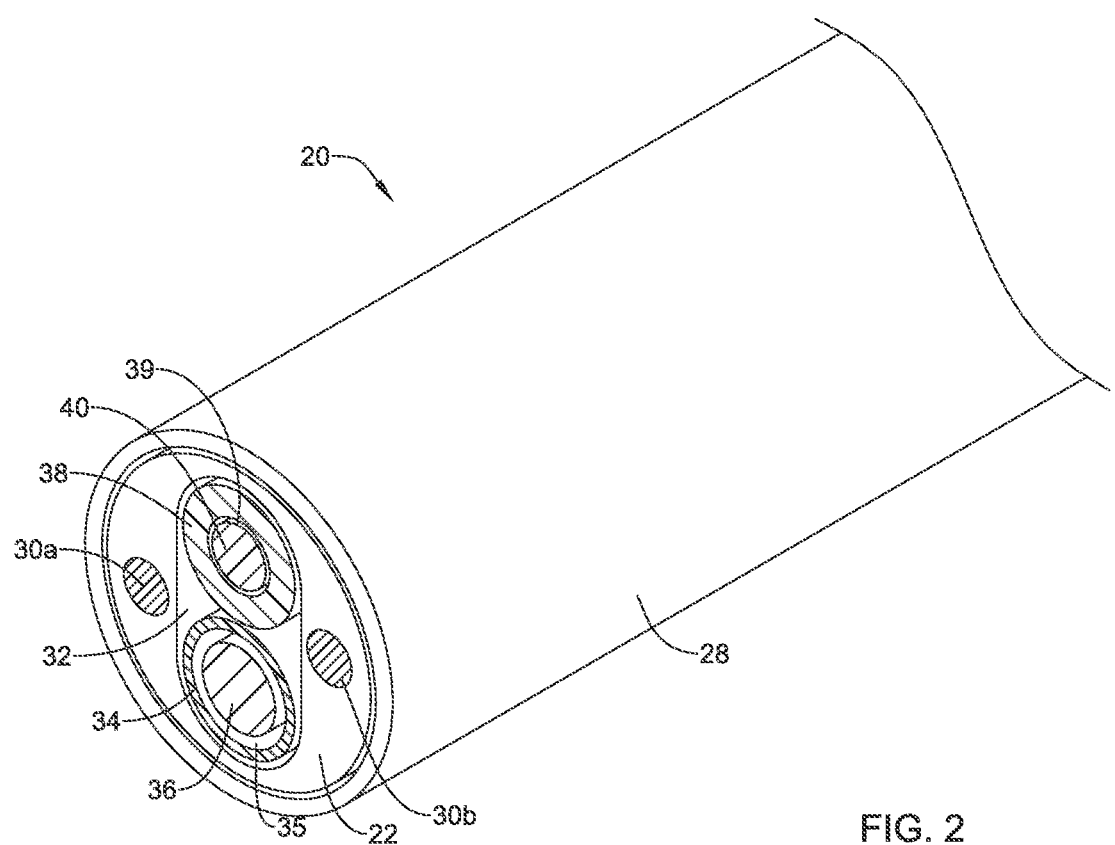
FIG. 2 is a perspective view of a portion of the shaft of the medical device shown in FIG. 1.

FIG. 2 illustrates a portion of an example shaft 20 that may that reduce the profile of portions of the medical device while maintaining sufficient strength (compressive, torsional, etc.) and flexibility of the system as a whole. In some instances, the shaft 20 may be used as the inner catheter 14 in the medical device system 10 illustrated in FIG. 1. However, the shaft 20 may be other components of the medical device system 10, a component of a different medical device system (e.g., a stent delivery system, an angioplasty system, a biopsy system, etc.), any other medical device where reduced profile designs may be required, or the like.

The shaft 20 may include an inner member or the liner 22. The inner liner 22 may include a number of features as discussed herein. An outer member 28 may be disposed along the outer surface of the inner liner 22. The outer member 28 may be designed to translate and/or rotate relative to the liner 22. For example, it can be appreciated that as the shaft 20 is advanced through the anatomy, the liner 22 may translate longitudinally or radially twist within the outer member 28.

The inner liner 22 may include a number of features. For example, the inner liner 22 may include one or more tension resistance members 30a/30b. The tension resistance members 30a/30b may take the form of a wire (e.g., a metallic wire), a braid, cable, stranded cable, a composite structure, or the like. In one example, the tension resistance members 30a/30b are both metallic wires. In another instance, the tension resistance members 30a/30b are both metallic braids. The braids may further includes an axial wire made from a suitable polymer or metal (e.g., aramid). The tension resistance members 30a/30b may be made from the same materials and/or have the same configuration. Alternatively, the tension resistance members 30a/30b may be different from one another. Furthermore, while FIG. 2 illustrates that the inner liner 22 includes two tension resistance members 30a/30b, this is not intended to be limiting. Other numbers of tension resistance members 30a/30b are contemplated such as one, three, four, five, six, seven, or more.

The inner liner 22 may also include a lumen 32. In some instances, a first tubular member 34 may be disposed within the lumen 32. The first tubular member 34 may define a guidewire lumen 35, through which a guidewire 36 may extend. A second tubular member 38 may also be disposed within the lumen 32. The second tubular member 38 may define a lumen 39 through which an actuation member 40 may extend. As described above, the actuation member 40 may be coupled and/or attached to the medical implant 16. Translation of the actuation member 40 may shift the implant 16 from a first collapsed configuration to a second deployed configuration.

Figure 3:
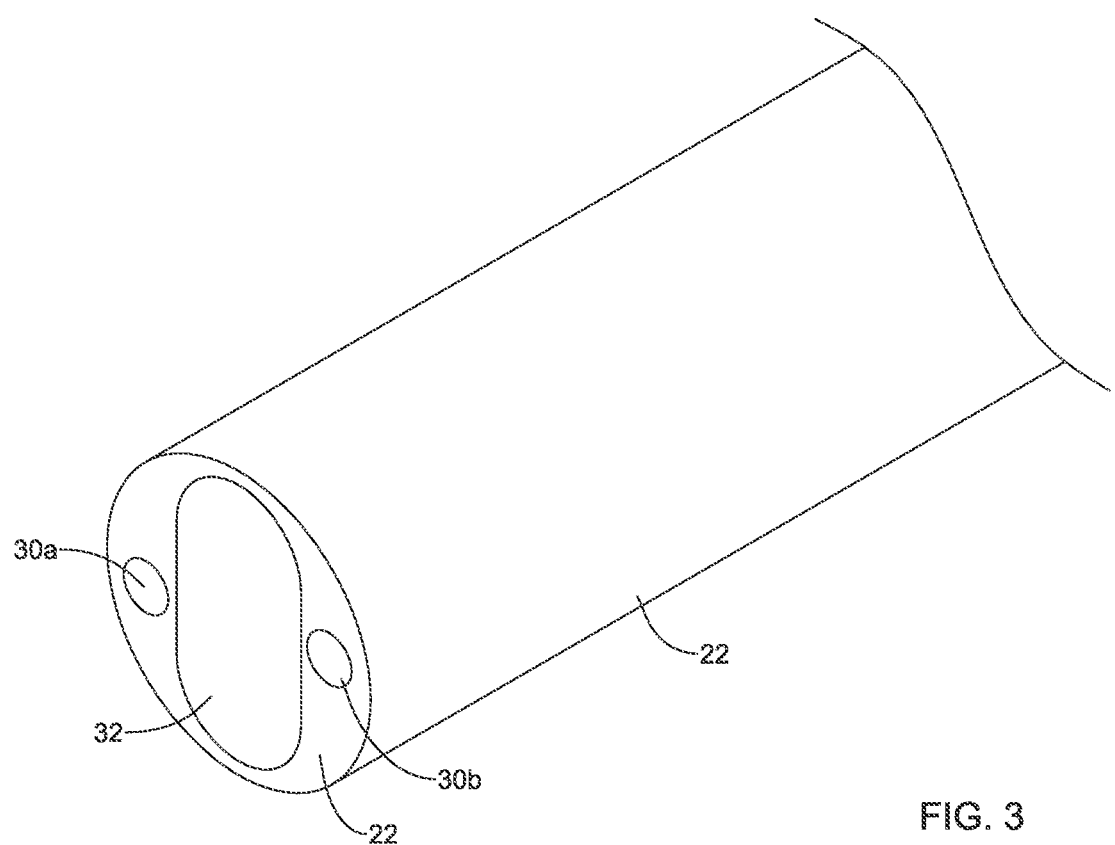
FIG. 3 is a perspective view of an example inner catheter of the medical device system shown in FIG. 1 and FIG. 2.

FIG. 3 illustrates the liner 22 described with respect to FIGS. 1-2. As shown in FIG. 3 and described above, the liner 22 may include a pair of tension resistance members 30a/30b which are positioned on opposite sides of the lumen 32. FIG. 3 further illustrates that the shape of the lumen 32 may be designed to limit twisting of the first tubular member 34 and the second tubular member 38 relative to one another. For example, FIG. 3 illustrates that the lumen 32 may be non-circular. For example, the shape of the lumen 32 may be ovular, square, rectangular, triangular, combinations thereof, etc. These are just examples. The inner liner 22 may vary in form. For example, the inner liner 22 may include various shapes in combination with a single lumen or multiple lumens. Further, the liner 22 may lack a lumen.

It can be appreciated that as the liner 22 rotates within the lumen of the outer member 28, the non-circular shape of the lumen 32 may force both the first tubular member 34 and the second tubular member 38 to maintain their respective spatial relationship as depicted in FIG. 2. In other words, the shape of the lumen 32 forces the first tubular member 34 and the second tubular member 38 to remain in their respective positions relative to one another independent of the bending, rotating, flexing, etc. of the liner 22.

While FIG. 2 illustrates that the lumen 32 is designed to accommodate a first tubular member 34 and a second tubular member 38, it is contemplated that the lumen 32 may be configured to accommodate more or less than two individual tubular members. For example, the lumen 32 may be shaped to accommodate one, two, three, four, five, six, seven, eight or more lumens. Further, it is contemplated that the particular shape of the lumen 32 may be designed to match the outer profile of any number of lumens collectively grouped together. For example, while not depicted in the figures, it can be appreciated that a triangular-shaped lumen 32 may match the outer profile of three circular tubular members grouped together at approximately 120 degrees offset from one another. This is not intended to be limiting. Rather, the lumen 32 may be shaped to match the profile of any collection of tubular members having any given outer profile. As discussed above, matching the shape of the lumen 32 with the profile of the tubular members positioned therein limits the ability of the tubular members from twisting around one another within the lumen 32.

It can be further appreciated that varying the shape of the lumen 32 may contribute to reducing the overall profile of the liner 22, and by extension, the overall profile of the shaft 20. For example, varying the shape of the lumen 32 may permit the reduction in the wall thickness separating individual lumens extending within the liner 22. Reducing the wall thickness separating the individual lumens may permit the overall profile of the liner 22 and/or the shaft 20 to be much smaller than existing liners/shaft designs.

Figure 4:
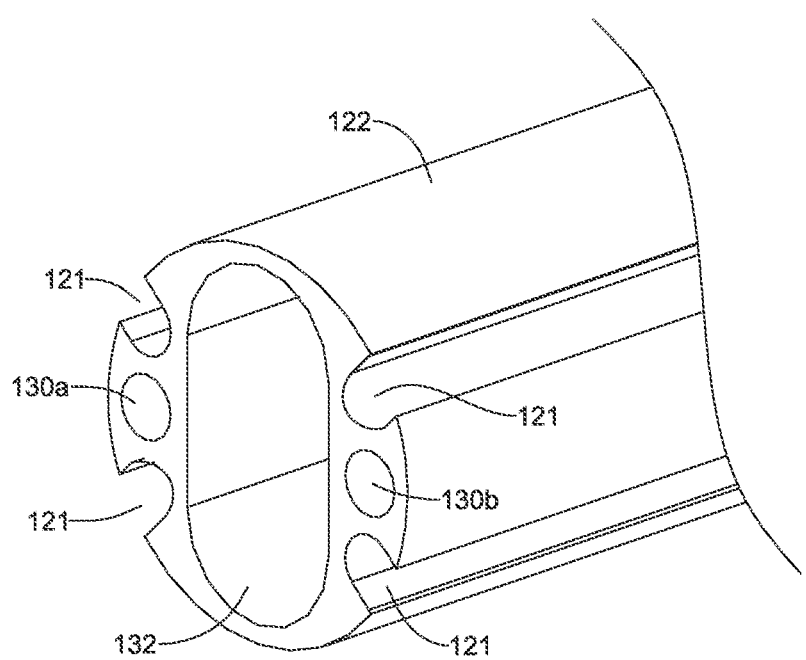
FIG. 4 is a perspective view of another example inner catheter of the medical device system shown in FIG. 1 and FIG. 2.

Additionally, it can be appreciated that it may be desirable to vary the shape of the profile of the outer surface of liner 22. For example, FIG. 4 illustrates another example liner 122. Liner 122 may be similar in form and function to other liners discussed herein. For example, liner 122 may include an inner lumen 132 and two tension resistance members 130a/130b. However, as shown in FIG. 4, liner 122 may also an outer surface profile that includes one or more longitudinally extending channels 121 (e.g., grooves, troughs, etc.) extending along the length thereof. As shown in FIG. 4, each of the channels 121 may include a curved portion that, in some examples, follows the profile of the inner lumen 132 and two tension resistance members 130a/130b.

Figure 5:
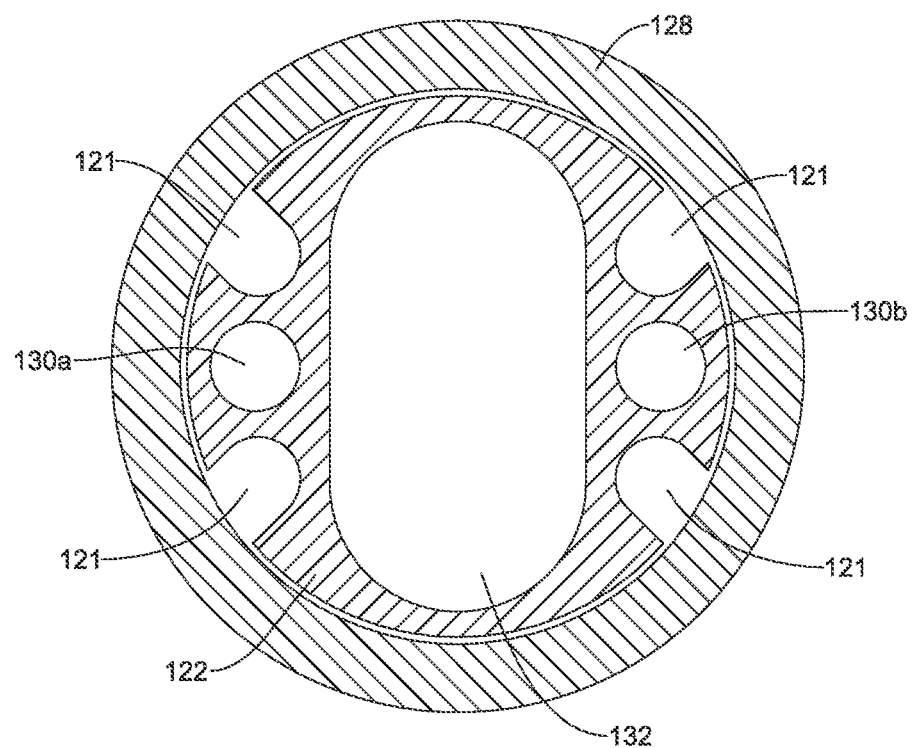
FIG. 5 is a cross-sectional view of the example inner catheter of the medical device system shown in FIG. 4.

FIG. 5 illustrates a cross-sectional view of the inner liner 122 shown in FIG. 4. However, FIG. 5 further illustrates an outer member 128 (which may be similar in form and function to outer member 28 discussed above) positioned over the inner liner 122. It can be appreciated from FIG. 5 that one or more of the channels 121 may create one or more "pseudo-lumens" (e.g., space, opening, aperture, etc.) extending the length of liner 122 and outer member 128 between the outer surface of inner liner 122 and the inner surface of outer member 128. In some instances, it may be desirable to extend (e.g., position) wires, cables, etc. through the channels 121. It is contemplated that the wires, cables, etc. which may be extended through channels 121 may be in addition to the two tension resistance members 130a/130b.

The materials that can be used for the various components of the medical devices and/or systems disclosed herein (e.g., shaft 20 and/or other shafts disclosed herein) may include those commonly associated with medical devices. For simplicity purposes, the following discussion makes reference to the shaft 20. However, this is not intended to limit the devices and methods described herein, as the discussion may be applied to other shafts and/or components of the medical devices and/or systems disclosed herein including the various bead members, barrel members, etc.

The shaft 20 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the shaft may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the shaft in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the shaft 20 to achieve the same result.

In some embodiments, a degree of Magnetic Resonance Imaging (Mill) compatibility is imparted into the shaft. For example, the shaft 20 may include a material that does not substantially distort the image and create substantial artifacts (e.g., gaps in the image). Certain ferromagnetic materials, for example, may not be suitable because they may create artifacts in an MRI image. The shaft 20 may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery system for an implantable medical device, comprising:
    an inner shaft having a proximal end region, a distal end region, a non-circular lumen extending therethrough, and at least one tension resistance member extending at least partially between the proximal end region and the distal end region and within the inner shaft;
    a first tubular member defining a guidewire lumen;
    at least one second tubular member defining an actuation member lumen;
    a deployment catheter disposed along an outer surface of the inner shaft; and
    an actuation member disposed within the actuation member lumen;
    wherein the first tubular member and the at least one second tubular member are received within the non-circular lumen;
    wherein the actuation member is coupled to an implantable medical device;
    wherein translation of the actuation member shifts the implantable medical device from a first position to a second position.

2. The delivery system of claim 1, wherein the implantable medical device includes an implantable heart valve.

3. The delivery system of claim 1, wherein the inner shaft includes a second tension resistance member and the at least one tension resistance member and the second tension resistance member are disposed along opposite sides of the inner shaft.

4. The delivery system of claim 1, further comprising one or more additional tubular members, each having an actuation member lumen, configured to receive an actuation member disposed within the non-circular lumen, and wherein the non-circular lumen is designed to limit twisting of tubular members within the non-circular lumen.

5. The delivery system of claim 1, wherein the inner shaft is configured to rotate, translate or both rotate and translate relative to the deployment catheter.

6. The delivery system of claim 1, wherein the non-circular lumen is designed to limit twisting of the first tubular member and the at least one second tubular member.

7. The delivery system of claim 1, wherein the at least one tension resistance member includes a metallic wire.

8. The delivery system of claim 1, wherein the at least one tension resistance member includes a polymer.

9. A delivery system for an implantable heart valve, comprising:
    an inner shaft having a distal end region, a proximal end region, an ovular lumen extending therethrough, and at least one tension resistance member extending at least partially between the proximal end region and the distal end region and within the inner shaft;
    a first tubular member defining a guidewire lumen;
    at least one second tubular member defining an actuation member lumen;
    a deployment catheter disposed along an outer surface of the inner shaft; and
    an actuation member disposed within the actuation member lumen;
    wherein the first tubular member and the at least one second tubular member are received within the ovular lumen;
    wherein the actuation member is configured to be coupled to an implantable heart valve;
    wherein translation of the actuation member shifts the implantable heart valve from a first position to a second position.

10. The delivery system of claim 9, wherein the inner shaft includes a second tension resistance member and the at least one tension resistance member and the second tension resistance member are disposed along opposite sides of the inner shaft.

11. The delivery system of claim 9, further comprising one or more additional tubular members, each having an actuation member lumen, configured to receive an actuation member disposed within the ovular lumen, and wherein the ovular lumen is designed to limit twisting of tubular members within the ovular lumen.

12. The delivery system of claim 9, wherein the ovular lumen is designed to limit twisting of the first tubular member and the at least one second tubular member.

13. The delivery system of claim 9, wherein the at least one tension resistance member includes a metallic wire.

14. The delivery system of claim 9, wherein the at least one tension resistance member includes a polymer.

* * * * *